US010350319B2

(12) United States Patent
Olson et al.

(10) Patent No.: US 10,350,319 B2
(45) Date of Patent: Jul. 16, 2019

(54) METHOD FOR LIQUID DETECTION AND DRYING

(71) Applicant: Sterilucent, Inc., Minneapolis, MN (US)

(72) Inventors: Steven J. Olson, Mahtomedi, MN (US); Kent A. Larson, Woodbury, MN (US); Jennifer M. Berg, Savage, MN (US); Dominique J. Megran, Dominique, MN (US)

(73) Assignee: Sterilucent, Inc., Minneapolis, MN (US)

( * ) Notice: Subject to any disclaimer, the term of this patent is extended or adjusted under 35 U.S.C. 154(b) by 360 days.

(21) Appl. No.: 15/413,022

(22) Filed: Jan. 23, 2017

(65) Prior Publication Data
US 2018/0207306 A1 Jul. 26, 2018

(51) Int. Cl.
| | |
|---|---|
| *A61L 2/20* | (2006.01) |
| *A61L 2/24* | (2006.01) |
| *F26B 5/04* | (2006.01) |
| *F26B 25/22* | (2006.01) |
| *B65B 55/10* | (2006.01) |
| *B65B 55/18* | (2006.01) |
| *B65B 55/02* | (2006.01) |
| *A61L 2/26* | (2006.01) |

(52) U.S. Cl.
CPC ............... *A61L 2/20* (2013.01); *A61L 2/202* (2013.01); *A61L 2/206* (2013.01); *A61L 2/208* (2013.01); *A61L 2/24* (2013.01); *A61L 2/26* (2013.01); *B65B 55/02* (2013.01); *B65B 55/10* (2013.01); *B65B 55/18* (2013.01); *F26B 5/04* (2013.01); *F26B 25/22* (2013.01); *A61L 2202/14* (2013.01); *A61L 2202/23* (2013.01); *A61L 2202/24* (2013.01)

(58) Field of Classification Search
CPC .......... A61L 2/20; A61L 2/24; A61L 2202/14; F26B 5/04; F26B 25/22
See application file for complete search history.

(56) References Cited

U.S. PATENT DOCUMENTS

| | | | |
|---|---|---|---|
| 5,317,896 | A | 6/1994 | Sheth et al. |
| 5,482,683 | A | 1/1996 | Sheth et al. |
| 5,961,922 | A | 10/1999 | Witte et al. |

(Continued)

FOREIGN PATENT DOCUMENTS

| | | |
|---|---|---|
| CN | 1175306 | 3/1998 |
| JP | 4062456 | 3/2008 |
| WO | 2010144106 | 12/2010 |

OTHER PUBLICATIONS

Notification of Transmittal of the International Search Report and the Written Opinion of the International Searching Authority, or the Declaration, Jul. 5, 2018.

*Primary Examiner* — Kevin Joyner
(74) *Attorney, Agent, or Firm* — DeWitt LLP; Thomas J. Nikolai

(57) ABSTRACT

Liquid water detection in a sterilization chamber that can distinguish liquid water from material in the load that is outgassing and can dry the liquid, is independent of the vacuum pump and chamber leak rate, and that is capable of detecting small amounts of liquid and drying the liquid without freezing the liquid in the process is achieved by monitoring conditions in the chamber at two different pressures, one above the boiling point of water and another below the boiling point of water at a given load temperature.

18 Claims, 10 Drawing Sheets

(56) References Cited

U.S. PATENT DOCUMENTS

| | | |
|---|---|---|
| 8,230,616 B2 | 7/2012 | McLaren et al. |
| 8,366,995 B2 | 2/2013 | McLaren et al. |
| 2015/0313250 A1 | 11/2015 | Itarashiki et al. |

Vapor Pressure of Water (0-100°C)

| T (°C) | T (°F) | P (kPa) | P (Torr) | P (atm) |
|---|---|---|---|---|
| 0 | 32 | 0.61 | 4.59 | 0.0060 |
| 5 | 41 | 0.87 | 6.55 | 0.0086 |
| 10 | 50 | 1.23 | 9.21 | 0.0121 |
| 15 | 59 | 1.71 | 12.79 | 0.0168 |
| 20 | 68 | 2.34 | 17.54 | 0.0231 |
| 25 | 77 | 3.17 | 23.77 | 0.0313 |
| 30 | 86 | 4.25 | 31.84 | 0.0419 |
| 35 | 95 | 5.63 | 42.20 | 0.0555 |
| 40 | 104 | 7.38 | 55.37 | 0.0728 |
| 45 | 113 | 9.59 | 71.93 | 0.0946 |
| 50 | 122 | 12.34 | 92.59 | 0.1218 |
| 55 | 131 | 15.75 | 118.15 | 0.1555 |
| 60 | 140 | 19.93 | 149.50 | 0.1967 |
| 65 | 149 | 25.02 | 187.68 | 0.2469 |
| 70 | 158 | 31.18 | 233.84 | 0.3077 |
| 75 | 167 | 38.56 | 289.25 | 0.3806 |
| 80 | 176 | 47.37 | 355.33 | 0.4675 |
| 85 | 185 | 57.82 | 433.65 | 0.5706 |
| 90 | 194 | 70.12 | 525.92 | 0.6920 |
| 95 | 203 | 84.53 | 634.02 | 0.8342 |
| 100 | 212 | 101.32 | 759.96 | 1.0000 |

David R. Lide, ed. (2005). CRC Handbook of Chemistry and Physics. Boca Raton, Florida: CRC Press. p. 6-8.

Fig. 3

Liquid-water Detection Method for a Variety of Load Conditions

| Wet Loads | Total Water [ml] | $(dP/dt)\|_{10\,Torr}$ [mTorr/s] | Comparison | $(dP/dt)\|_{90\,Torr}$ [mTorr/s] | Result |
|---|---|---|---|---|---|
| Petri Dish with 3.00 ml Water | 3.00 | 38.86 | > | 19.06 | WET |
| Petri Dish with 2.00 ml Water | 2.00 | 34.74 | > | 16.28 | WET |
| Petri Dish with 1.00 ml Water | 1.00 | 34.49 | > | 13.35 | WET |
| Petri Dish with 0.50 ml Water | 0.50 | 19.74 | > | 7.18 | WET |
| Petri Dish with 0.25 ml Water | 0.25 | 8.01 | > | 4.98 | WET |
| Petri Dish with 0.10 ml Water | 0.10 | 5.40 | > | 4.62 | WET |
| 2 Petri Dishes with 0.05 ml Water Each | 0.10 | 6.38 | > | 4.22 | WET |
| Petri Dish with 0.05 ml Water | 0.05 | 3.34 | > | 2.94 | WET |
| 2 Petri Dishes with 0.05 ml Water Each + 1 Aesculap Mat | 0.10 | 11.56 | > | 9.68 | WET |
| Petri Dish with 2.00 ml Water, 25 lb Case with 1 Aesculap Mat | 2.00 | 37.41 | > | 19.06 | WET |
| Petri Dish with 1.00 ml Water, 25 lb Case with 1 Aesculap Mat | 1.00 | 13.13 | > | 10.64 | WET |
| Petri Dish with 0.50 ml Water, 25 lb Case with 2 Plasma-tazz® Mats | 0.50 | 16.60 | > | 15.66 | WET |
| Dry Loads | Total Water [ml] | $(dP/dt)\|_{10\,Torr}$ [mTorr/s] | Comparison | $(dP/dt)\|_{90\,Torr}$ [mTorr/s] | Result |
| Empty Chamber | 0.00 | 0.39 | ≤ | 1.12 | DRY |
| 1 Aesculap Mat | 0.00 | 5.50 | ≤ | 6.11 | DRY |
| 2 Aesculap Mats | 0.00 | 11.25 | ≤ | 13.40 | DRY |
| 3 Aesculap Mats | 0.00 | 13.49 | ≤ | 17.10 | DRY |
| 4 Aesculap Mats | 0.00 | 14.94 | ≤ | 15.93 | DRY |
| 25 lb Case with 1 Aesculap Mat | 0.00 | 4.55 | ≤ | 6.05 | DRY |
| 2 Plasma-tazz® Mats | 0.00 | 7.30 | ≤ | 9.02 | DRY |
| Empty Case with 2 Plasma-tazz® Mats | 0.00 | 3.52 | ≤ | 6.60 | DRY |
| 2 Steri-Cel™ Mats | 0.00 | 2.09 | ≤ | 4.15 | DRY |
| Empty Case with 2 Steri-Cel™ Mats | 0.00 | 2.59 | ≤ | 5.63 | DRY |

Plasma-tazz® is a registered trademark of General Hospital Supply Corporation of Monroe, North Carolina.
Steri-Cel™ is a trademark of Healthmark Industries Company Corporation of Frasier, Michigan.

Fig. 5

METHOD FOR LIQUID DETECTION AND DRYING

FIELD OF THE INVENTION

The present invention relates to the detection and removal of liquid in a vacuum chamber and, more particularly, to the detection and removal of liquid water in a sterilization chamber that employs a gas-phase chemical sterilant.

BACKGROUND OF THE INVENTION

The presence of liquid water in a vacuum chamber can be detrimental to many vacuum processes. This is particularly the case for gas-phase chemical sterilization chambers as the presence of liquid water can inhibit sterilization at surface locations where the liquid water is located.

In practice, items to be sterilized (the sterilization load) should be thoroughly cleaned and dried prior to sterilization. A chemical gas-phase sterilization process proceeds as follows: the sterilization load is placed into a vacuum chamber and a sealing door is closed; a vacuum pump removes the atmosphere within the chamber to a medium vacuum level; the chamber is closed from the vacuum pump with a valve and a chemical gas or vapor sterilant in added to the chamber; the low pressure in the chamber allows the sterilant gas to flow and diffuse throughout the sterilization load, killing spores, viruses and bacteria on the surfaces of the sterilization load; after a suitable exposure period, the sterilant gas is removed from the chamber through the vacuum pump; air is vented back into the chamber to return the system to atmospheric pressure; finally, the sterilized sterilization load is removed.

There are many types of gas-phase chemical sterilants that may be used including, hydrogen peroxide, ethylene oxide, ozone, chlorine dioxide, combinations of these sterilants and others. In particular, hydrogen peroxide is a highly effective vapor-chemical sterilant that can be applied at low temperatures allowing temperature sensitive articles to be processed in the load. Note: a gaseous-chemical sterilant and a vapor-chemical sterilant both utilize the sterilant in gas-phase, but a vapor-chemical sterilant could exist with solid and/or liquid phase sterilant at the temperature of the sterilization process, while a gaseous-chemical sterilant is purely in gas phase. The following U.S. patents, incorporated fully herein by reference, describe such a system and sterilization process in more detail: U.S. Pat. No. 8,230,616 issued Jul. 31, 2012 to McLaren et al. and U.S. Pat. No. 8,366,995 issued Feb. 5, 2013 to McLaren et al.

While the sterilization load should be thoroughly cleaned and dried prior to sterilization, sometimes the load will not be entirely dry. A sterilization load may comprise many items including items with lumens or other channels or crevices that are difficult to dry and may contain liquid water.

As noted above, water in the load can be detrimental to chemical gas sterilization in several ways. Issues may arise due to the higher diffusivity of water compared to the sterilant. This is the case for hydrogen peroxide where the water vapor may reach portions of the load before hydrogen peroxide vapor and diminish the effectiveness of the sterilization action. Other issues may arise if the liquid water remains throughout the sterilization process in either liquid or solid form. The water can block the sterilant gas from contacting portions of the load surfaces, whether they are external surfaces, or internal surfaces such as lumens. In fact, at the operating pressures for chemical sterilization, liquid water can freeze with little chance of removal during the sterilization process.

Several methods have been employed to try to detect liquid water in a load, and to try and remove the liquid water from the load prior to sterilization. U.S. Pat. No. 5,317,896 issued Jun. 7, 1994 to Sheth and Upchurch and U.S. Pat. No. 5,482,683 issued Jan. 9, 1996 to Sheth and Upchurch each describe a detection method using the pump-down time from a pressure above the saturation pressure of water to a pressure below the saturation pressure of water. This pump-down time is compared to a reference pump-down time for a dry system. A longer pump-down would indicate the presence of water. U.S. Pat. No. 5,961,922 issued Oct. 5, 1999 to Witte and Eulogio describes an alternative method in which the pressure is monitored during pump-down below 5 Torr. If water is present, the pressure data often increases for small time periods as the water freezes at the surface and bursts or breaks the ice as the pressure decreases. U.S. Pat. No. 8,230,616 issued Jul. 31, 2012 to McLaren et al., discloses a third water detection method that involves a pump-down to a pre-determined pressure, at which time the pump-down is stopped and the pressure rise is monitored. If the rise is below a threshold value, the load is dry. If the rise is above the threshold, additional steps are taken to attempt to dry the load prior to sterilization.

Each of the methods described above have disadvantages. Simply monitoring the pump-down time will give results that are dependent on the effectiveness of the pump and the integrity of the chamber, both of which are subject to change over time. In addition, the load materials may outgas at varying degrees depending on the load. The materials outgas water vapor, and vapors from oils, greases, solvents, and volatile organics most commonly. Monitoring the pressure below 5 Torr may be a better approach. However, not all liquid water distributions will exhibit an increasing pressure during the monitoring period, so loads with liquid water may be missed and the liquid water may freeze. Finally, monitoring the pressure rise and comparing to a threshold value can work, but may give false indications of water in the load, if the load has a large enough amount of outgassing material. This would trigger additional and unnecessary drying procedures.

It would, therefore, be advantageous to provide a method that is capable of determining whether the load contains liquid water even if the load contains material that is outgassing water vapor and that dries the load in a reliable and verifiable way.

It would also be advantageous to provide a method that detects liquid water in a load that is independent of vacuum pump variations and the underlying chamber leak rate and that dries the load in a reliable and verifiable way.

It would further be advantageous to provide a method that is capable of detecting small amounts of liquid water in a load, without freezing the liquid water and that dries the load in a reliable and verifiable way.

SUMMARY OF THE INVENTION

In accordance with the present invention, there is provided a method for liquid water detection in a sterilization chamber that can distinguish liquid water from material in the load that is outgassing water vapor, that is independent of the vacuum pump and chamber leak rate, and that is capable of detecting small amounts of liquid water without freezing the liquid water and that dries the load in a reliable and verifiable way.

BRIEF DESCRIPTION OF THE DRAWINGS

FIG. 3 is a table showing the vapor pressure of water at various temperatures;

FIG. 4 is an example pressure versus time plot following the method described in FIG. 2a;

FIG. 5 is a table illustrating the results of various tests of the methods and apparatus described herein;

DETAILED DESCRIPTION OF THE INVENTION

Figure 1:
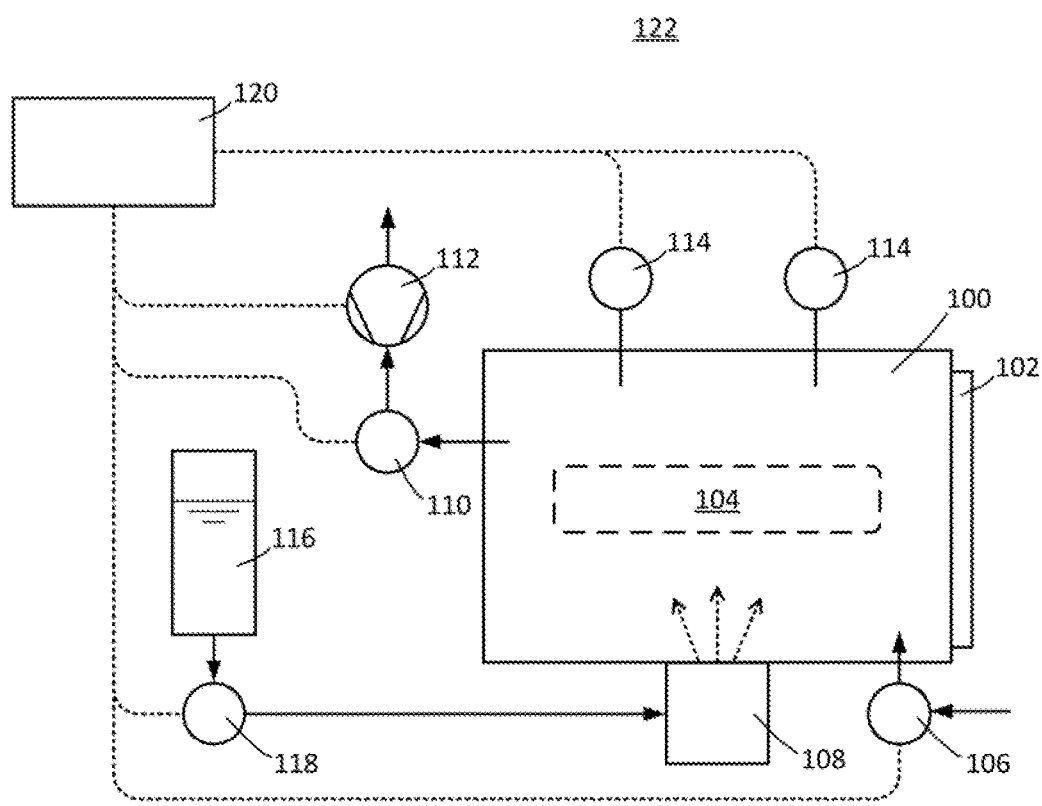
FIG. 1 is a block diagram representation of a chemical-vapor sterilization system.

Referring now to the invention in more detail, in FIG. 1 there is shown a block diagram for a vapor-chemical sterilization system that employs a sterilant like hydrogen peroxide. Note: a gaseous-chemical sterilant and a vapor-chemical sterilant both utilize the sterilant in gas-phase, but a vapor-chemical sterilant could exist with solid and/or liquid phase sterilant at the temperature of the sterilization process, while a gaseous-chemical sterilant is purely in gas phase. The sterilization process is conducted in a sterilization chamber 100. The interior of the sterilization chamber 100 is accessible through a chamber door 102 that may open with a hinge, a sliding mechanism, or by other means, which can be closed to provide a substantially airtight seal with the sterilization chamber 100. Both the sterilization chamber 100 and the chamber door 102 are typically metallic with stainless steel or aluminum as common material choices. The sterilization chamber 100 and the chamber door 102 are typically heated to 35-55° C. when hydrogen peroxide is used as the sterilant, but may be heated to different temperatures or unheated for other sterilant gases.

Prior to sterilization, the items to be sterilized are thoroughly cleaned and dried. By way of example, these items may include any of a variety of medical, surgical or dental instruments, lumen devices including stainless steel and plastic tubes, rigid scopes, flexible scopes and other items that must be used under sanitary and germ free conditions. After the items are cleaned and dried, the items are then packaged. The packaging will include cushions and supports to protect the items to be sterilized and a gas-permeable wrap or container to house the items and cushions.

Packaging can be done in a variety of ways, but all packaging includes a gas-permeable layer or filter that allows the sterilant gas or vapor to contact items to be sterilized within the packaging. The gas-permeable materials, however, do not allow the package to be penetrated by spores, viruses and bacteria after sterilization that would contaminate the articles rendering them no longer sterile. Packaging materials include Tyvek® pouches, trays and baskets that are overwrapped with a sterilization wrap like KimGuard®, and sterilization containers such as Genesis® containers, among other types. Tyvek® is a registered trademark of E. I. du Pont de Nemours and Company of Wilmington, Del. KimGuard® is a registered trademark of Kimberly-Clark Worldwide, Inc. of Neenah, Wis. Genesis® is a registered trademark of CareFusion 2200 Corporation of San Diego, Calif.

A sterilization load 104 is comprised of one or more packages of items to be sterilized. The sterilization load 104 is placed inside the sterilization chamber 100 through the chamber door 102. The sterilization load 104 is typically placed on an open rack within the sterilization chamber 100 which allows sterilant to access all portions of the sterilization load 104.

An inlet valve 106 isolates the sterilization chamber 100 from the surrounding ambient air 122. The inlet valve 106 may be either normally-open, normally-closed, or a variably opening valve type. It is preferable to use a normally-open, solenoid valve for the inlet valve 106 that can be controlled by a controller 120. A normally-open valve type allows the sterilization chamber 100 to vent back to atmospheric pressure if power to the system is lost for any reason.

One or more pressure sensor(s) 114 are connected to the sterilization chamber 100 and monitored by the controller 120. The pressure sensor(s) 114 should be capable of measuring the pressure inside the sterilization chamber 100 with sufficient accuracy to resolve pressure increases due to water and outgassing from the sterilization load 104. Capacitance manometers work well in this application, as their reading is independent of the type of gas within the sterilization chamber 100.

A vacuum pump 112 is connected to the sterilization chamber 100 through a vacuum valve 110. The vacuum valve 110 may be either normally-open, normally-closed, or a variably opening valve type. It is preferable to use a normally-closed, solenoid valve that can be controlled by the controller 120 for the vacuum valve 110. A normally-closed valve type prevents backflow from the vacuum pump 112 if power to the system is lost for any reason. The vacuum pump 112 is preferably a dry vacuum pump, such as a roots type blower, with its operation controllable by controller 120. A dry vacuum pump 112 eliminates concern for oil back-flowing into the sterilization chamber 100, or polluting the ambient air 122 with oil mist.

Sterilant is contained in a sterilant source 116, which is coupled to a vaporizer 108, through a sterilant valve 118. The vaporizer 108 is sealed and fluidly connected to the sterilization chamber 100. It is preferably heated to a temperature above the sterilization chamber 100 temperature and of sufficient heat capacity to fully vaporize the sterilant liquid entering it. The sterilant source 116 contains sufficient sterilant for a sterilization run. The sterilant valve 118 isolates the sterilant source 116 from the vaporizer 108. The sterilant valve 118 may be either normally-open, normally-closed, or a variably opening valve type. It is preferable to use a normally-closed, solenoid valve that can be controlled through a controller 120 for the sterilant valve 118. A normally-closed valve prevents sterilant from flowing to the vaporizer 108 if the system loses power.

The process can be controlled manually, but it is preferable to control the entire sterilization process with a controller 120. Controller 120 may take many forms, but is preferably a microprocessor based system with firmware designed specifically for this application. The controller controls the inlet valve 106, the vacuum valve 110, the sterilant valve 118 and the vacuum pump 112 and monitors system sensors including pressure sensor(s) 114.

A simple sterilization process using the system represented by the block diagram of FIG. 1 to sterilize a fully dry sterilization load 104 proceeds as follows: (1) the sterilization load 104 is placed inside the sterilization chamber 100 through the chamber door 102 which is then closed; (2) inlet valve 106 is closed, vacuum pump 112 is started and vacuum valve 110 is opened to start the chamber evacuation process; (3) pressure sensor(s) 114 monitor the pressure inside the sterilization chamber 100 until a predetermined sterilization pressure level is reached, typically in a range between 0.1 and 3 Torr and most typically ~1 Torr; (4) upon reaching the required pressure, vacuum valve 110 is closed to isolate the sterilization chamber 100 at vacuum; (5) the sterilant valve 118 is opened for a predetermined period so that sterilant is drawn out of the sterilant source 116 and routed to the vaporizer 108 by the vacuum level within the sterilization chamber 100; (6) the sterilant is vaporized in the vaporizer 108 and the vapor surrounds the sterilization load 104 inside the sterilization chamber 100; (7) after a sufficient period of time to affect sterilization of the sterilization load 104, the vacuum valve 110 is opened and any sterilant vapor in the sterilization chamber 100 is removed from the system through the vacuum pump 112; (8) the vacuum valve 110 is closed and inlet valve 106 is opened to allow ambient air 122 to vent into the sterilization chamber 100, bringing the pressure back to atmospheric pressure; and (9) the chamber door 102 is opened and the sterilization load 104 is removed from the sterilization chamber 100.

The sterilization process described above is very simple and an actual sterilization process may include more steps and equipment not included in this description. U.S. Pat. No. 8,366,995 issued Feb. 5, 2013 to McLaren et al. and incorporated herein describes such a sterilization process with additional equipment including filters and sterilant concentration sensors, and additional steps, including multiple injections, venting steps and multiple exposures. In particular, the sterilization process may include water detection methods and the cycle may be canceled, or move into a load-drying phase if water is detected in the sterilization load.

Figure 2A:
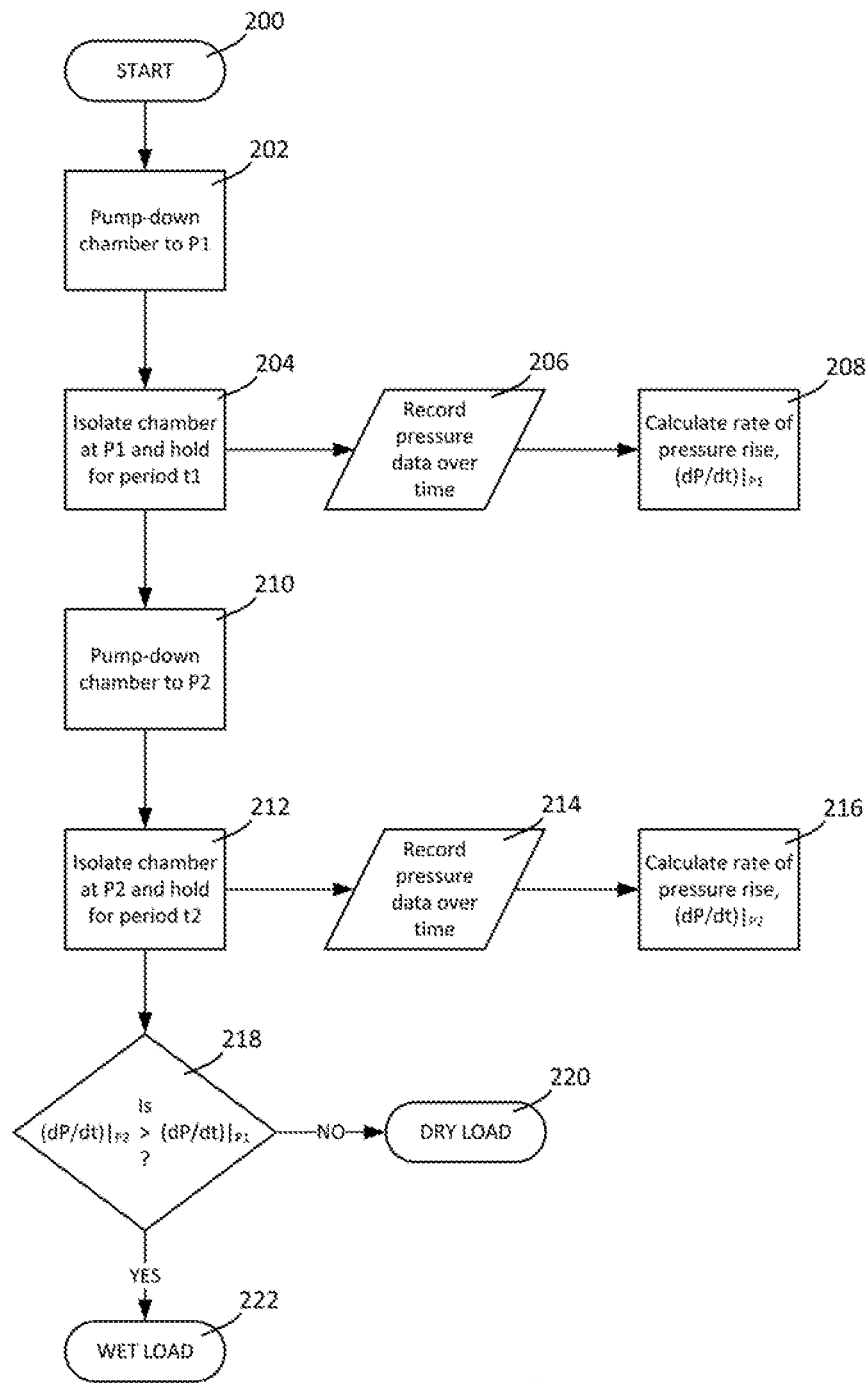
FIG. 2a is a flowchart for the liquid-water detection method.

FIG. 2a provides a flowchart for a liquid-water detection method. The process start 200 signifies the start of a sterilization cycle. A sterilization cycle often begins with a pre-conditioning phase and includes all the steps prior to sterilant injection. A first pump-down 202 follows to a first predetermined pressure $P_1$. When the pressure $P_1$ is reached, a first chamber isolation 204 begins. The system is isolated for a first predetermined period of time, $t_1$. During this period, a first pressure record 206 is made. The pressure record 206 is a record of the pressure inside the chamber over time. The pressure record 206 is created by periodically recording during the first chamber isolation 204 pressure data including a pressure measurement of the pressure in the chamber and the time the pressure measurement is taken. Following the creation of the first pressure record 206, a first rate of pressure rise 208 is determined from the data. A second pump-down 210 follows to a second predetermined pressure $P_2$. When the pressure $P_2$ is reached, a second chamber isolation 212 begins. The system is isolated for a second predetermined period of time, $t_2$. During this period, a second pressure record 214 is made. The pressure record 214 is also a record of the pressure inside the chamber over time. The pressure record 214 is created by periodically recording throughout the second chamber isolation 212 pressure data including a pressure measurement of the pressure in the chamber and the time the pressure measurement is taken. Following the creation of the second pressure record 214, a second rate of pressure rise 216 is determined from the data. Finally, a comparison 218 of the first rate of pressure rise 208 is made with the second rate of pressure rise 216. If the first rate of pressure rise 208 is larger than the second rate of pressure rise 216, then system has a dry load 220. If the first rate of pressure rise 208 is less than or equal to the second rate of pressure rise 216, then the system has a wet load 222.

The pressure $P_1$ is preferably above the vapor pressure of water, while pressure $P_2$ is preferably below the vapor pressure of water at the sterilization load 104 temperature. FIG. 3 below gives the vapor pressure of water from 0 to 100° C. The goal is to select a pressure for $P_1$ at which liquid water does not boil and a pressure for $P_2$ at which liquid water does boil. In this way, the rate of water vapor generated at the lower pressure ($P_2$), will be greater than the rate of water vapor generated at the higher pressure ($P_1$). The vapor generation rate translates into a pressure increase rate that is easily measured with a suitable pressure sensor(s) 114.

Figure 2B:
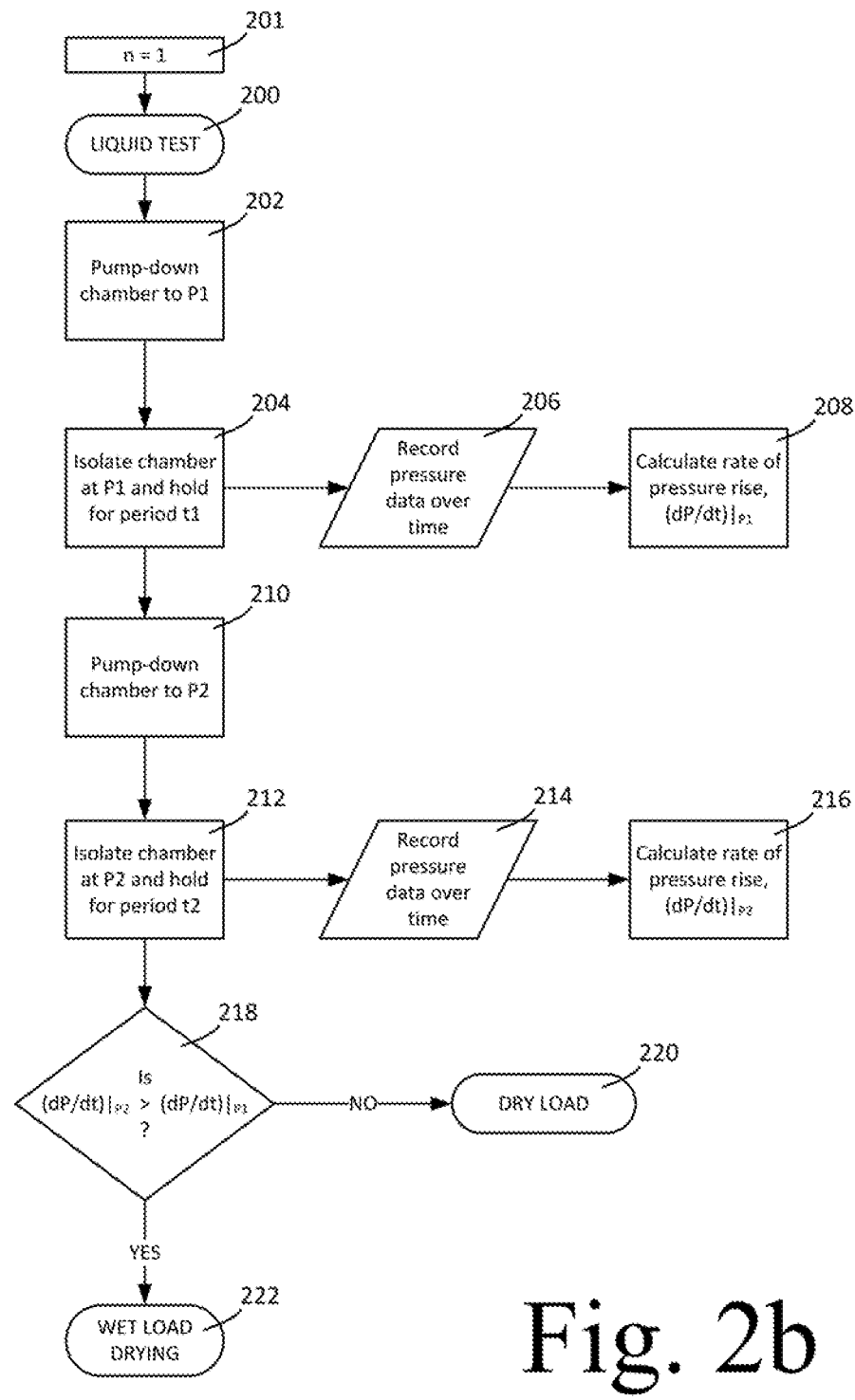
FIG. 2b is a flowchart for the liquid-water detection method that includes a counter when drying the load.

FIG. 2b provides a flowchart for a liquid-water detection and drying method. Before the process is started, a drying attempt counter 201 is initialized. The process start 200 signifies the start of a sterilization cycle. A sterilization cycle often begins with a pre-conditioning phase and includes all the steps prior to sterilant injection. A first pump-down 202 follows to a first predetermined pressure $P_1$. When the pressure $P_1$ is reached, a first chamber isolation 204 begins. The system is isolated for a first predetermined period of time, $t_1$. During this period, a first pressure record 206 is made. Following the creation of the first pressure record 206, a first rate of pressure rise 208 is determined from the data. A second pump-down 210 follows to a second predetermined pressure $P_2$. When the pressure $P_2$ is reached, a second chamber isolation 212 begins. The system is isolated for a second predetermined period of time, $t_2$. During this period, a second pressure record 214 is made. Following the creation of the second pressure record 214, a second rate of pressure rise 216 is determined from the data. Next, a comparison 218 of the first rate of pressure rise 208 is made with the second rate of pressure rise 216. If the first rate of pressure rise 208 is larger than the second rate of pressure rise 216, then system has a dry load 220. If the first rate of pressure rise 208 is less than or equal to the second rate of pressure rise 216, then the system has a wet load 222 and the cycle moves on to additional steps to dry the load.

The table of FIG. 3 shows the pressures for $P_1$ and for $P_2$ that may be used at various temperatures. For example, if the load has a temperature equal to room temperature, or 20° C., a pressure above and below 17.54 Torr would be chosen as reflected in the table of FIG. 3. Using a pressure sensor(s) 114 with a maximum reading of 100 Torr, a selection of $P_1$=90 Torr and $P_2$=10 Torr works well. At 90 Torr, liquid water will not boil until nearly 50° C., while at 10 Torr, liquid water can boil at slightly above 10° C. Choosing a lower pressure, particularly below about 5 Torr, will cause any liquid water in the sterilization load 104 to quickly freeze. This is problematic for several reasons: the sublimation rate from frozen water is much lower than the vaporization rate during boiling, so the presence of liquid water (now frozen) will be missed; if drying steps will be attempted when liquid water is detected, allowing the liquid water to freeze will slow the process as the frozen water will need to be melted before significant drying can occur.

Figure 4:
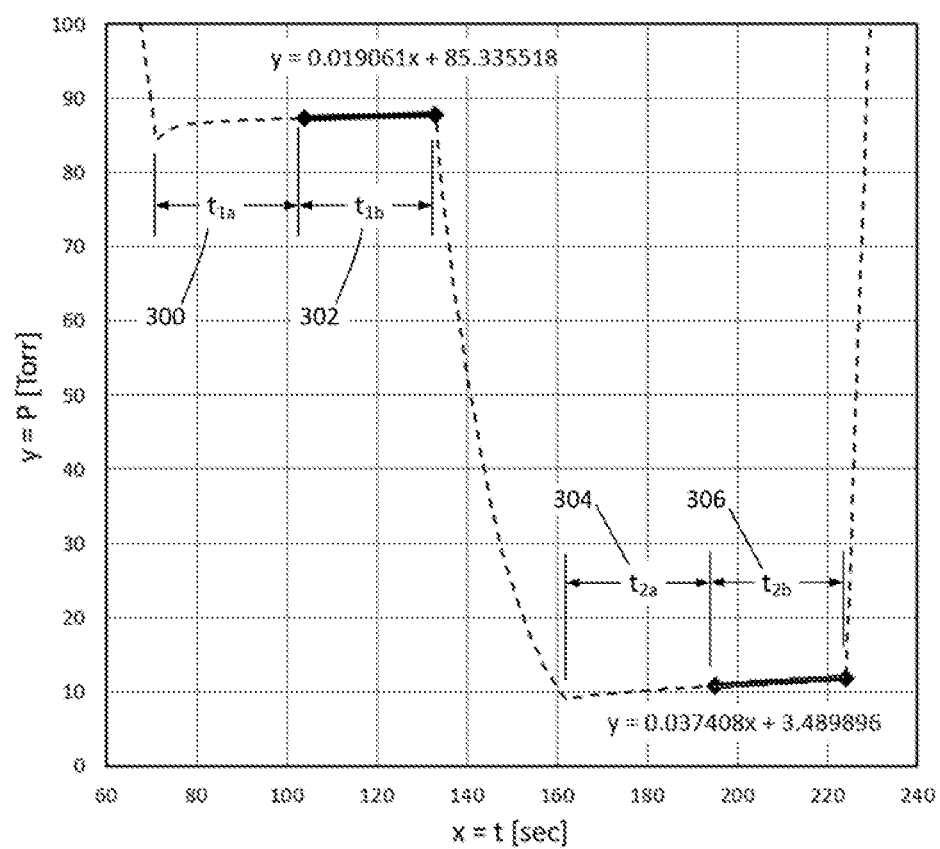

FIG. 4 shows an example of the water detection method described in the flowchart of FIG. 2a. In this particular test, a Genesis® case with 25 lb of stainless steel surgical instruments and a silicone mat together with a Petri dish containing 2 ml of liquid water was used as the sterilization load 104. FIG. 4 shows the pressure data below 100 Torr. At approximately 90 Torr ($P_1$), the sterilization chamber 100 was isolated from the vacuum pump 112 by closing the vacuum valve 110. This corresponds to the first chamber isolation 204 of the water detection flowchart. The pressure was held for 60 seconds ($t_1$) before opening the vacuum valve 110. A second pump-down to approximately 10 Torr ($P_2$) was conducted and the vacuum valve 110 was again closed. The pressure was held for 60 seconds ($t_2$) before opening the inlet valve 106 to vent the chamber back to atmospheric pressure.

As shown in FIG. 4, the holding time periods ($t_1$ and $t_2$) are divided into two portions:

$$t_1 = t_{1a} + t_{1b}$$

$$t_2 = t_{2a} + t_{2b}$$

The first holding period is comprised of two periods: a first transient period 300 signified by $t_{1a}$; and a first correlation period 302 signified by $t_{1b}$. The second holding period is also comprised of two periods: a second transient period 304 signified by $t_{2a}$; and; a second correlation period 306 signified by $t_{2b}$. The first transient period 300 and the second transient period 304 ($t_{1a}$ and $t_{2a}$) are intended to span any transient measurement data that occurs due to the pressure sensor dynamics, or the atmosphere stabilization in the sterilization chamber that occurs when the vacuum valve is suddenly closed. The first correlation period 302 and second correlation period 306 ($t_{1b}$ and $t_{2b}$) are the portions over which a curve-fits to the pressure data are made. For the test shown in FIG. 4, all of the time intervals ($t_{1a}$, $t_{1b}$, $t_{2a}$, $t_{2b}$) were 30 seconds long. Other time intervals could be used and there is no requirement that any of them be equal. It is preferable to choose $t_{1a}$ and $t_{2a}$ to be as short as possible, but long enough to exceed any transient effects of the sensor dynamics or atmosphere stabilization. The time intervals for curve-fitting ($t_{1b}$ and $t_{2b}$) are also preferably as short as possible, but long enough to produce a meaningful slope from the test data.

The data collected during $t_{1b}$ and $t_{2b}$ are independently fit to straight lines using regression analysis. Linear least-squares solutions are used in this case to solve for the slopes of the lines through the pressure data over time. For the test case in FIG. 4, the slope of the pressure data over the time interval $t_{1b}$ is 0.019061 Torr/sec, while the slope of the pressure data over the time interval $t_{2b}$ is 0.037407 Torr/sec. Since, $(dP/dt)|_{10\ Torr} > (dP/dt)|_{90\ Torr}$ (or, 0.037407>0.019061), this indicates that liquid water is present in the load.

Examples

Figure 6:
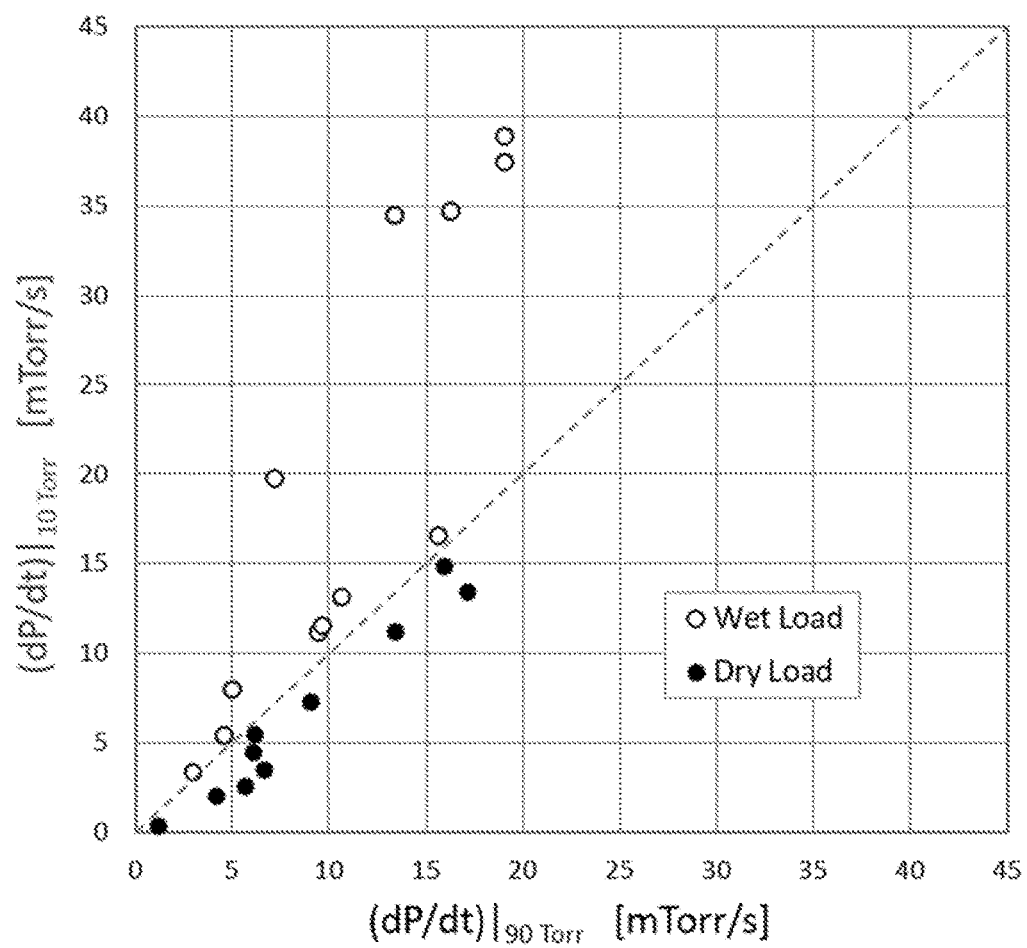
FIG. 6 is a plot showing the pressure rise rate at lower pressure versus the pressure rise rate at higher pressure for the tests in FIG. 5.

A series of tests was conducted to illustrate the liquid-water detection method for a variety of load conditions. FIG. 5 below summarizes the test data. For these tests, a consistent set of pressures and time intervals was used: $P_1$=90 Torr, $P_2$=10 Torr, $t_1$=60 sec, $t_2$=60 sec, and $t_{1a}$=$t_{1b}$=$t_{2a}$=$t_{2b}$=30 sec. The data is also presented as a plot in FIG. 6. In this plot, a diagonal line indicates the condition where $(dP/dt)|_{10\ Torr}$=$(dP/dt)|_{90\ Torr}$. Data that falls above this diagonal line indicates liquid water in the load according to the algorithm in FIG. 2a. Data that falls on or below the diagonal line indicates a dry load according to the algorithm in FIG. 2a. It can be seen that the liquid-water detection algorithm of FIG. 2a has correctly identified each of the test loads in the table of FIG. 5 and as shown FIG. 6.

Figure 7:
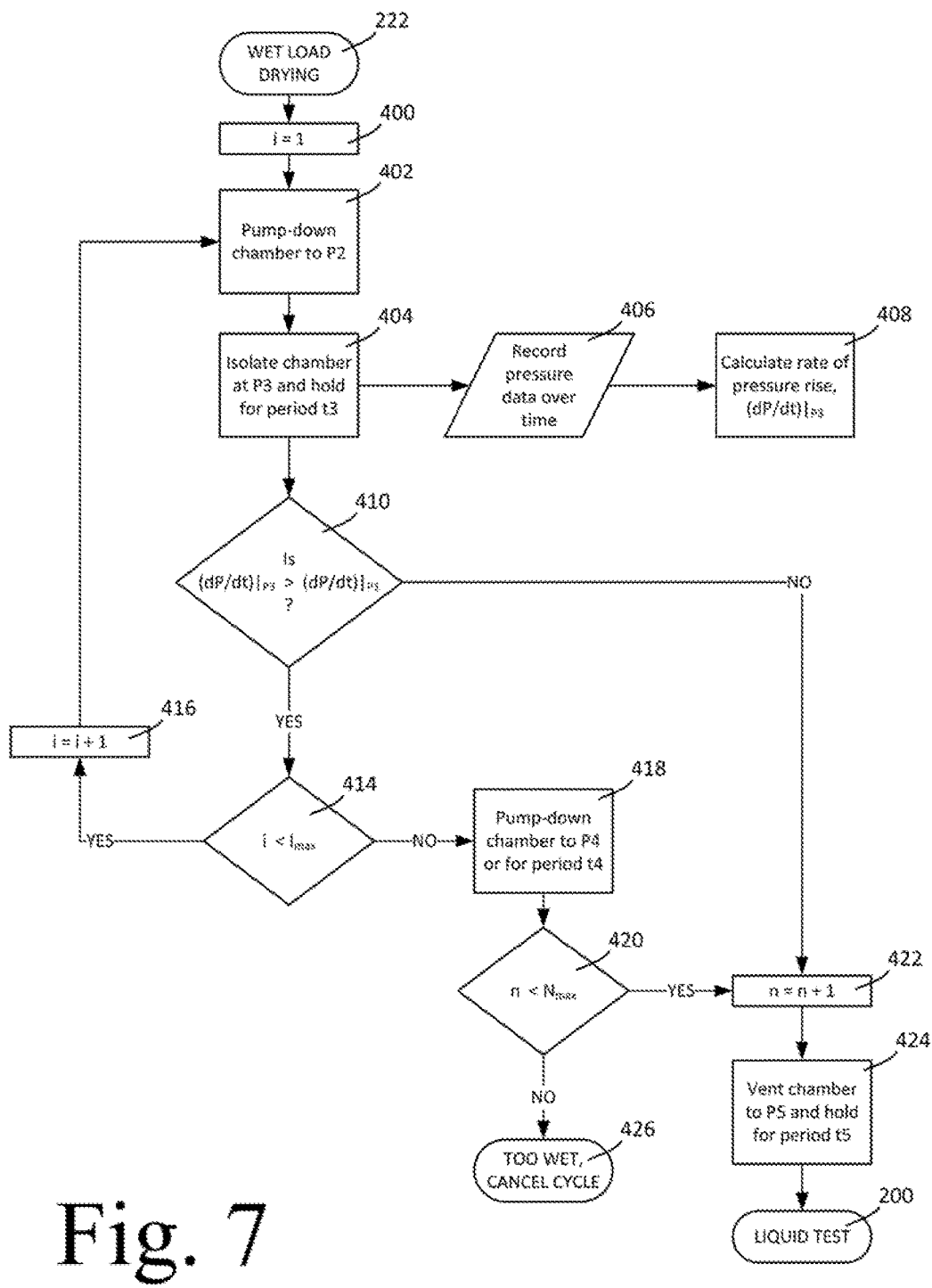
FIG. 7 is a flowchart for the liquid drying method.

When liquid water is detected in the sterilization load, a load drying routine may be undertaken to dry the sterilization load. FIG. 7 gives a flowchart for drying the load when liquid water is detected. The process begins when a Wet Load 222 is detected using the algorithm of FIG. 2b. An iteration counter 400 is initialized to 1 and the chamber is pumped-down 402 to $P_3$ and held for a period of time $t_3$. During this time period, the pressure is recorded 406 and a calculation of the pressure rise at $P_3$ 408 is made in the manner described in FIG. 4. A comparison 410 of the pressure rise rate at $P_3$ is made to the pressure rise rate at $P_1$ (determined earlier during the algorithm in FIG. 2b).

If the pressure rise rate at $P_1$ is greater than or equal to the pressure rise rate at $P_3$, the iteration steps for this drying attempt are halted and the drying attempt counter is incremented by 1 422. The chamber is vented to $P_5$ 424 and held for a time period $t_5$ to allow any frozen liquid in the load to melt, prior to an additional liquid test 200 as verification that the load is dry. If the comparison 410 indicates that the pressure rise rate at $P_3$ is greater than the pressure rise rate at $P_1$, an iteration counter is checked 414 to see if the maximum number of iterations has been reached. If the maximum number if iterations has not been reached, the iteration counter is incremented 416 and the chamber is pumped down to $P_3$ 402 and held for a period $t_3$ again. If the maximum number of iterations has been reached, the chamber is pumped down to $P_4$ 418, or for a period $t_4$ (whichever occurs first). This evacuation step removes liquid water, but can cause the water to freeze, so it is terminated if $t_4$ is reached. Following this evacuation, the number of drying attempts is checked against the maximum number of drying attempts 420. If the number of drying attempts is less than the maximum number of attempts, the drying attempt counter 422 is incremented. The chamber is vented to $P_5$ 424 and held for a period $t_5$ to allow any frozen liquid in the load to melt, prior to an additional liquid test 200 to check if the load is dry. If the maximum number of drying attempts has been exceeded 420, the load is considered too wet and the cycle is canceled 426.

Figure 8:
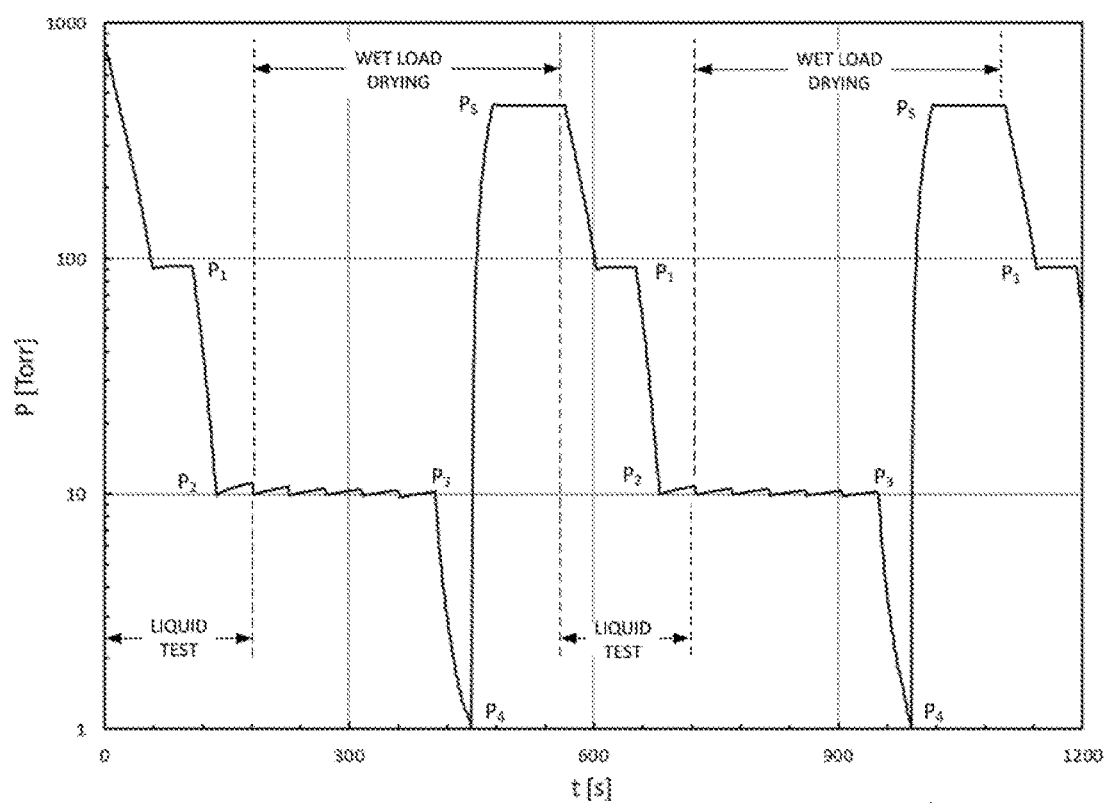
FIG. 8 is an example pressure versus time plot following the method described in FIG. 7.
Figure 9:
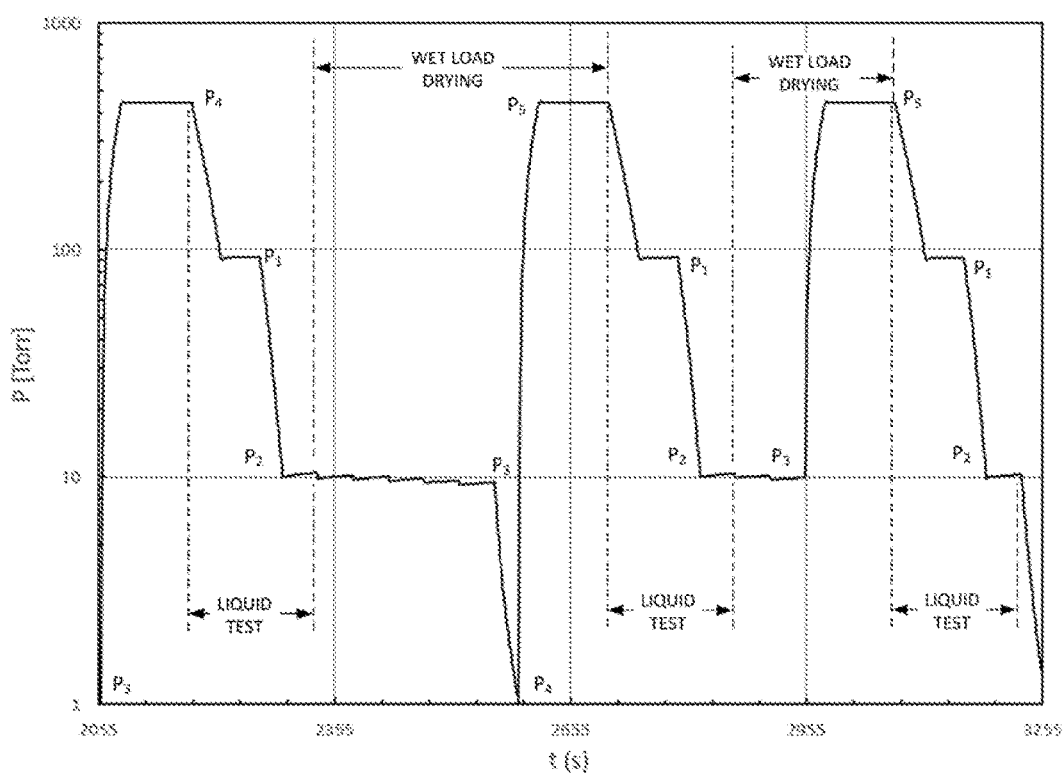
FIG. 9 is a further example pressure versus time plot following the method described in FIG. 7.

FIGS. 8 and 9 give an example of liquid water detection method of FIG. 2b and the drying method of FIG. 7. FIG. 8 shows the beginning of the drying and FIG. 9 shows the end of the drying for the same test. This particular test had a sterilization load that included a plastic Petri dish with 2 mL of liquid water in it. The parameters for the test are: $P_1$=90 Torr; $P_2$=$P_3$=10 Torr; $P_4$=1 Torr, $t_4$=60 sec; $P_5$=450 Torr, $t_5$=90 sec; $I_{max}$=5, $N_{max}$=10.

FIG. 8 shows data from the beginning of the test. The chamber is evacuated from atmospheric pressure down to $P_1$ (90 Torr), where the pressure rise rate is determined. From there it is evacuated to $P_2$ (10 Torr), where the second pressure rise rate is determined. The pressure rise rate at $P_2$ is greater than the pressure rise rate at $P_1$, so the load contains liquid water. This ends the first liquid test. Note: the pressure is presented on a logarithmic scale, so the pressure rise rate at $P_1$ appears less than the pressure rise rate at $P_2$, but it is not.

The load is wet, so the system moves on to its drying algorithm. The chamber is evacuated to $P_3$ (10 Torr) and the pressure rise rate is calculated and compared to the original pressure rise rate at $P_1$ (90 Torr). This is repeated for the maximum number of iterations (5 in this test). The load is still wet, so the chamber is evacuated to $P_4$ (1 Torr). Upon reaching $P_4$, the chamber is vented to $P_5$ (450 Torr) and held for $t_5$ (90 sec) to increase heat transfer to the load and melt any ice that may have formed during the earlier evacuations. This ends the first drying attempt.

FIG. 8 also shows a complete second Liquid Test and Wet Load Drying sequence. The only difference in this set is that the initial evacuation for the Liquid Test is from $P_5$ (450 Torr) rather than from atmospheric pressure (nominally 760 Torr).

FIG. 9 shows the same test in FIG. 8 at a later time. The first liquid test shown in FIG. 9 is actually the fifth liquid test in this cycle. It indicates the load is wet and is followed by a full sequence of drying steps, similar to those in FIG. 8. The next liquid test indicates the load is still wet. The cycle moves on to the wet load drying. In this case, the pressure rise rate at $P_3$ (10 Torr) is less than the pressure rise rate at $P_1$ (90 Torr) on the second iteration, so additional iterations are skipped and the algorithm moves on to a final vent to $P_5$ (450 Torr) to warm the load and melt any ice that may have formed. The liquid test now indicates that the pressure rise rate at $P_2$ is less than the pressure rise rate at $P_1$, so the load is dry. The evacuation at the end is an evacuation to the pressure level for the first sterilant injection.

The advantages of the present invention include, without limitation, the ability of the method to detect liquid water in the load and to distinguish liquid water from material in the load that is outgassing and to dry the load. In addition, the method is independent of the vacuum pump and chamber leak rate, and is useful for varied loads and for system's whose performance characteristics change over time. Also, the method is capable of detecting and drying small amounts of liquid without freezing the liquid in the process and is therefore suitable for liquid water detection in sterilization loads.

Variations of this method are envisioned that include, but are not limited to: (a) use for gas-phase chemical sterilants other than hydrogen peroxide, whether they are purely gaseous-chemical sterilants, or vapor-chemical sterilants; (b) methods that use sensors other than pressure sensors to detect the rate of water vapor evolution over time, including humidity sensors, optical absorption sensors and other sensors; (c) other methods beyond linear least-squares regression analysis to characterize the water vapor evolution over time; and (d) using more than two pressure levels in the analysis.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

What is claimed:

1. A method for determining whether a sterilization load is wet comprising the steps of:
    a. evacuating a chamber to first pressure, said first pressure being both sub-atmospheric and above the vapor pressure of water at the temperature of the load;
    b. isolating the chamber at the first pressure for a first predetermined time period comprising a first transient period and a first correlation period following the first transient period;
    c. during the first predetermined time period periodically recording pressure data including a pressure measurement of the pressure in the chamber and the time the pressure measurement is taken;
    d. calculating a first rate of pressure rise during the first correlation period using the pressure data periodically recorded during the first predetermined time period;
    e. further evacuating the chamber to a second pressure, said second pressure being below the vapor pressure of water at the temperature of the load;
    f. isolating the chamber at the second pressure for a second predetermined time period comprising a second transient period and a second correlation period following the second transient period;
    g. during the second predetermined time period periodically recording pressure data including a pressure measurement of the pressure in the chamber and the time the pressure measurement is taken;
    h. calculating a second rate of pressure rise during the second correlation period using the pressure data periodically recorded during the second predetermined time period; and
    i. comparing the second rate of pressure rise to the first rate of pressure rise, and identifying the load not too wet for sterilization to proceed if the second rate of pressure rise is below the first rate of pressure rise.

2. The method of claim 1 wherein the temperature of the load is below 50° C., the first pressure is 90 Torr and the second pressure is 10 Torr.

3. The method of claim 1 wherein the first pressure and the second pressure are each above the pressure at which water in the load will freeze given the temperature of the load.

4. The method of claim 1 wherein the first transient period and the second transient period are each long enough to span any transient pressure data that occurs due to the dynamics of equipment used to determine and record the pressure in the chamber.

5. The method of claim 1 wherein the first transient period and the second transient period are each long enough to span any transient measurement data that occurs due to the dynamics of equipment used to isolate the chamber at the first pressure and the second pressure.

6. The method of claim 1 wherein the first rate of pressure rise during the first correlation period is calculated by dividing the change in pressure during the first correlation period by the change in time during the first correlation period, and the second rate of pressure rise during the second correlation period is calculated by dividing the change in pressure during the second correlation period by the change in time during the second correlation period.

7. The method of claim 1 wherein the first rate of pressure rise and the second rate of pressure rise are independently determined by independently fitting pressure data recorded during the first correlation period and the pressure data recorded during the second correlation period to straight lines using regression analysis to determine the slopes of the lines through the pressure data over time.

8. The method of claim 7 wherein the step of comparing the second rate of pressure rise to the first rate of pressure rise is performed by comparing the slopes of the two lines.

9. A method for determining whether a sterilization load is wet and sterilizing the load if the load is not too wet to sterilize comprising the steps of:
    j. determining whether the load not too wet to sterilize by:
        i. evacuating chamber to a first pressure, said first pressure being both sub-atmospheric and above the vapor pressure of water at the temperature of the load;

ii. isolating the chamber at the first pressure for a first predetermined time period comprising a first transient period and a first correlation period following the first transient period;
iii. during the first predetermined time period periodically recording pressure data including a pressure measurement of the pressure in the chamber and the time the pressure measurement is taken;
iv. calculating a first rate of pressure rise during the first correlation period using the pressure data periodically recorded during the first predetermined time period;
v. further evacuating the chamber to a second pressure, said second pressure being below the vapor pressure of water at the temperature of the load;
vi. isolating the chamber at the second pressure for a second predetermined time period comprising a second transient period and a second correlation period following the second transient period;
vii. during the second predetermined time period periodically recording pressure data including a pressure measurement of the pressure in the chamber and the time the pressure measurement is taken;
viii. calculating a second rate of pressure rise during the second correlation period using the pressure data periodically recorded during the second predetermined time period;
ix. comparing the second rate of pressure rise to the first rate of pressure rise, and identifying the load as not too wet for sterilization to proceed if the second rate of pressure rise is below the first rate of pressure; and
k. sterilizing the load if the load is not too wet to sterilize by:
i. isolating the chamber at a predetermined sterilization pressure;
ii. admitting gaseous sterilant into the chamber;
iii. allowing the gaseous sterilant to diffuse throughout the chamber for a sterilization period sufficiently long to effect sterilization;
iv. after the sterilization period removing the sterilant from the chamber;
v. allowing air to vent into the chamber to raise the pressure in the chamber; and
vi. removing the load from the chamber.

10. The method of claim 9 wherein the predetermined sterilization pressure between 0.1 Torr and 3 Torr.

11. The method of claim 9 wherein at least one capacitance manometer is used to measure pressure within the chamber.

12. The method of claim 9 wherein the load comprises at least one item to be sterilized that has been packaged in packaging that includes a gas-permeable layer that permits the sterilant to pass through the packaging to contact the at least one item to be sterilized and prevents spores, viruses and bacteria to pass through the packaging.

13. The method of claim 9 wherein the method is carried out under the direction of an electronic controller.

14. The method of claim 9 wherein the gaseous sterilant is a pure gaseous sterilant.

15. The method of claim 9 wherein the gaseous sterilant is a vaporized compound.

16. The method of claim 9 wherein the gaseous sterilant is a vaporized mixture.

17. The method of claim 9 wherein the gaseous sterilant comprises hydrogen peroxide.

18. A method for determining whether a load is not too wet to sterilize, drying the load if the load is too wet to sterilize, and sterilizing the load if the load is not too wet to sterilize comprising the steps of:
l. determining whether the load is too wet to sterilize by:
i. evacuating a chamber to first pressure, said first pressure being both sub-atmospheric and above the vapor pressure of water at the temperature of the load;
ii. isolating the chamber at the first pressure for a first predetermined time period comprising a first transient period and a first correlation period following the first transient period;
iii. during the first predetermined time period periodically recording pressure data including a pressure measurement of the pressure in the chamber and the time the pressure measurement is taken;
iv. calculating a first rate of pressure rise during the first correlation period using the pressure data periodically recorded during the first predetermined time period;
v. further evacuating the chamber to a second pressure, said second pressure being below the vapor pressure of water at the temperature of the load;
vi. isolating the chamber at the second pressure for a second predetermined time period comprising a second transient period and a second correlation period following the second transient period;
vii. during the second predetermined time period periodically recording pressure data including a pressure measurement of the pressure in the chamber and the time the pressure measurement is taken;
viii. calculating a second rate of pressure rise during the second correlation period using the pressure data periodically recorded during the second predetermined time period;
ix. comparing the second rate of pressure rise to the first rate of pressure rise, and identifying the load as not too wet for sterilization to proceed if the second rate of pressure rise is below the first rate of pressure rise;
m. drying the load if the load is too wet to sterilize by:
i. evacuating the chamber to a third pressure;
ii. isolating the chamber at the third pressure for a third predetermined time period comprising a third transient period and a third correlation period following the third transient period;
iii. during the third predetermined time period periodically recording pressure data including a pressure measurement of the pressure in the chamber and the time the pressure measurement is taken;
iv. calculating a third rate of pressure rise during the third correlation period using the pressure data periodically recorded during the third predetermined time period;
v. comparing the third rate of pressure rise to the first rate of pressure rise and determining whether steps b.i. though b.v. have been performed a first predetermined maximum number of times;
vi. if the third rate of pressure rise is not below the first rate of pressure rise and steps b.i. though b. v. have not been performed the first predetermined maximum number of times, then repeating steps b.i. through b.v.;
vii. if the third rate of pressure rise is not below the first rate of pressure rise and steps b.i. though b. v. have been performed the first predetermined maximum number of times, then evacuating the chamber to a fourth predetermined pressure and then venting the chamber to a fifth predetermined pressure for a fifth predetermined period of time to allow any liquid that may have frozen to melt and returning to step a. if step b. vii. has not been performed a second predetermined maximum number of times and otherwise aborting;

viii. if the third rate of pressure rise is below the first rate of pressure rise and steps b.i. though b. v. have not been performed the first predetermined maximum number of times, then venting the chamber to a fifth predetermined pressure for a fifth predetermined period of time to allow any liquid that may have frozen to melt and then repeating step a to verify the load is dry enough to sterilize;

n. sterilizing the load if the load is not too wet to sterilize by:
  i. isolating the chamber at a predetermined sterilization pressure;
  ii. drawing gaseous sterilant into the chamber;
  iii. allowing the gaseous sterilant to diffuse throughout the chamber for a sterilization period sufficiently long to effect sterilization;
  iv. after the sterilization period removing the sterilant from the chamber;
  v. allowing air to vent into the chamber to raise the pressure in the chamber; and removing the load from the chamber.

* * * * *